United States Patent [19]
Koreeda et al.

[11] Patent Number: 5,414,074
[45] Date of Patent: May 9, 1995

[54] SYNTHESIS OF C-GLYCOSYLATED COMPOUNDS WITH THE USE OF A MILD, IODINE-CATALYZED REACTION

[75] Inventors: Masato Koreeda; Todd A. Houston, both of Ann Arbor, Mich.

[73] Assignee: University of Michigan, Ann Arbor, Mich.

[21] Appl. No.: 951,529

[22] Filed: Sep. 25, 1992

[51] Int. Cl.$^6$ .............. C07H 1/00; C07H 15/04; C07G 3/00
[52] U.S. Cl. .................. 536/18.6; 536/1.11; 536/4.1; 536/6.4
[58] Field of Search ............ 536/1.11, 18.6, 4.1, 536/6.4

[56] References Cited

U.S. PATENT DOCUMENTS

| | | | |
|---|---|---|---|
| 4,713,447 | 12/1987 | Letton | 536/18.6 |
| 4,871,837 | 10/1989 | Magnusson et al. | 536/4.1 |
| 5,003,057 | 3/1991 | McCurry et al. | 536/4.1 |

OTHER PUBLICATIONS

Hacksell, Daves, Jr., *Prog. Med. Chem.,* 1985, vol. 22, pp. 1–65, 1985.
Daves, Jr., *Acc. Chem. Res.,* vol. 23, pp. 201–206, 1990.
Dawe, Fraser–Reid, *J.C.S. Chem. Comm.,* pp. 1180–1181, 1981.
Sparks, *J. Org. Chem.,* vol. 47, pp. 3805–3806, 1982.
Sabol, Cregge, *Tetrahedron Lett.,* vol. 30, pp. 6271–6274, 1982.
Herscovici, Muleka, Antonakis, *Tetrahedron Lett.,* vol. 25, pp. 5653–5656, 1984.
Hacksell, Daves, Jr., *J. Org. Chem.,* vol. 48, pp. 2870–2876, 1983.

*Primary Examiner*—Herbert J. Lilling
*Attorney, Agent, or Firm*—Young, MacFarlane & Wood

[57] ABSTRACT

The invention concerns C-glycosylated derivatives of soft carbon nucleophile compounds, particularly compounds which contain acid-labile structural units. The invention further concerns a mild, cost-effective, non-hazardous and stereoselective method of general application employing a glycal as a glycosyulating agent and iodine as a catalyst for the preparation of C-glycosylated soft carbon nucleophile compounds.

4 Claims, No Drawings

SYNTHESIS OF C-GLYCOSYLATED COMPOUNDS WITH THE USE OF A MILD, IODINE-CATALYZED REACTION

FIELD OF THE INVENTION

The invention concerns C-glycosylated derivatives of soft carbon nucleophile compounds, particularly compounds which contain acid-labile structural units, and more particularly, C-glycosylated derivatives of known compounds that are useful pharmacological agents such as antibiotics, antineoplastic compounds and antiviral compounds. The invention further concerns a mild, cost-effective, non-hazardous and stereoselective method of general application employing a glycal as a glycosylating agent and iodine as a catalyst for the preparation of C-glycosylated soft carbon nucleophile compounds.

BACKGROUND OF THE INVENTION

A large number of drugs that exhibit potent antibiotic, antitumor and/or antiviral activity belong to the structural class of compounds known as C-glycosides, in which a carbohydrate moiety is attached to a carbon atom of a typically hydrophobic aglycon unit. Although their glycons are not particularly hydrophobic, C-nucleosides are the most representative of these C-glycosides both in their abundance and in their biological activities. Numerous C-glycosides are currently on the market as medicinal drugs. Therefore, development of an improved method for the synthesis of such compounds, especially their structural analogs that may possess enhanced pharmacological profiles, continues to be an area of intense commercial interest in the pharmaceutical and chemical industry (for reviews, see: Hacksell, U.; Daves, G. D., Jr. *Prog. Med. Chem.* 1985, 22, 1–65 and Daves, G. D., Jr. *Acc. Chem. Res.* 1990, 23, 201–206 both incorporated herewith by reference).

While several reactions that utilize glycal derivatives as glycosylating reagents have been reported employing various Lewis acids as catalysts for C-glycosylation, the harsh nature of these Lewis acids has prevented their application to the synthesis of the C-glycosylated derivatives of acid-labile substrates. These Lewis acids include boron trifluoride etherate (Dawe, R. D.; Fraser-Reid, B. *J.C.S. Chem. Commun.* 1981, 1180–1181; Panek, J. S.; Sparks, M. A. *J. Org. Chem.* 1982, 47, 3805–3806; Sabol, J. S.; Cregge, R. J. *Tetrahedron Lett.* 1989, 30, 6271–6274), ethyldichloroaluminum, and trimethylsilyl trifluoromethanesulfonate (for the use of both of these Lewis acids, see: Herscovici, J.; Muleka, K.; Antonakis, K. *Tetrahedron Lett.* 1984, 25, 5653–5656). In addition, since most of these strong Lewis acids spontaneously react with air and moisture, the use of these Lewis acids presents serious problems in their handling, particularly under the large-scale, industrial setting. Another approach to C-glycosylation that employs a glycal derivative requires the use of expensive metal catalyst whose effects to human health could potentially be serious drawbacks (Hacksell, U.; Daves, G. D., Jr. *J. Org. Chem.* 1983, 48, 2870–2876).

SUMMARY AND DETAILED DESCRIPTION

In one preferred aspect, the invention concerns C-glycoside compounds, as C-1α and C-1β epimer compounds, obtained by reacting a soft carbon nucleophile compound and a glycosylating agent selected from 3-acylated, carbonated and thionocarbonated five- and six-membered glycals in the presence of a catalytic amount of iodine (5–50 mol % with 20 mol % being the most representative) to provide a reaction mixture containing the corresponding C-1α and C-1β C-glycoside epimers, isolating at least one or both of said α and β epimers stereoselectively from said mixture, and optionally removing one or more acyl groups from said epimer products.

The use of the non-toxic, stable catalyst iodine, which is an extremely mild Lewis acid and yet according to the invention retains enough acidity to effect C-glycosylation, has virtually solved the heretofore difficult problems of the art.

For glycosylation, glycals of the formulas I–III and Ia–IIIa are preferred:

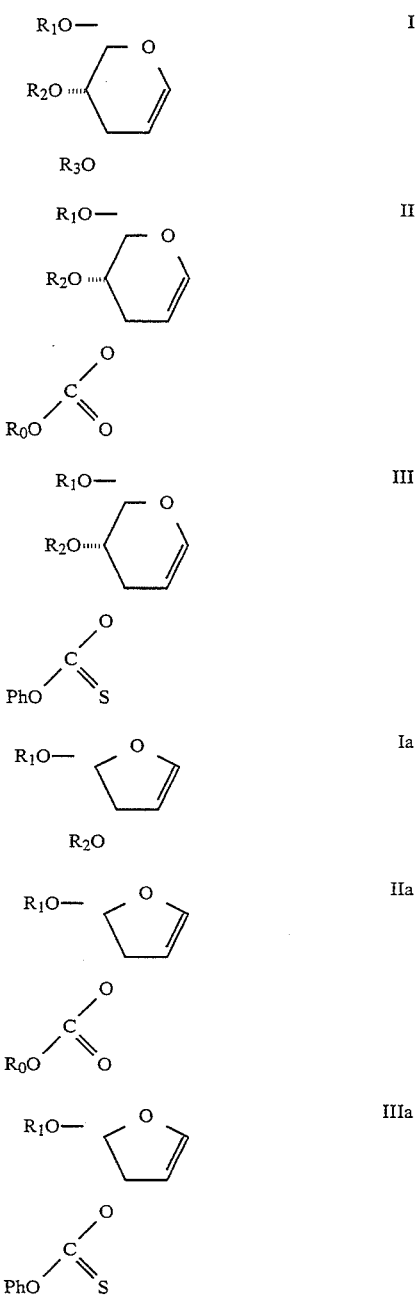

where $R_0$ is a lower alkyl group and $R_1$, $R_2$ and $R_3$ are the same or different and represent an aliphatic acyl group or an aromatic acyl group such as a benzoyl group. The glycals are commonly available or can be prepared by known methods.

Preferred soft carbon nucleophiles comprise a compound or a moiety selected from members of the group consisting of enolate derivatives having the formulas a) to w)

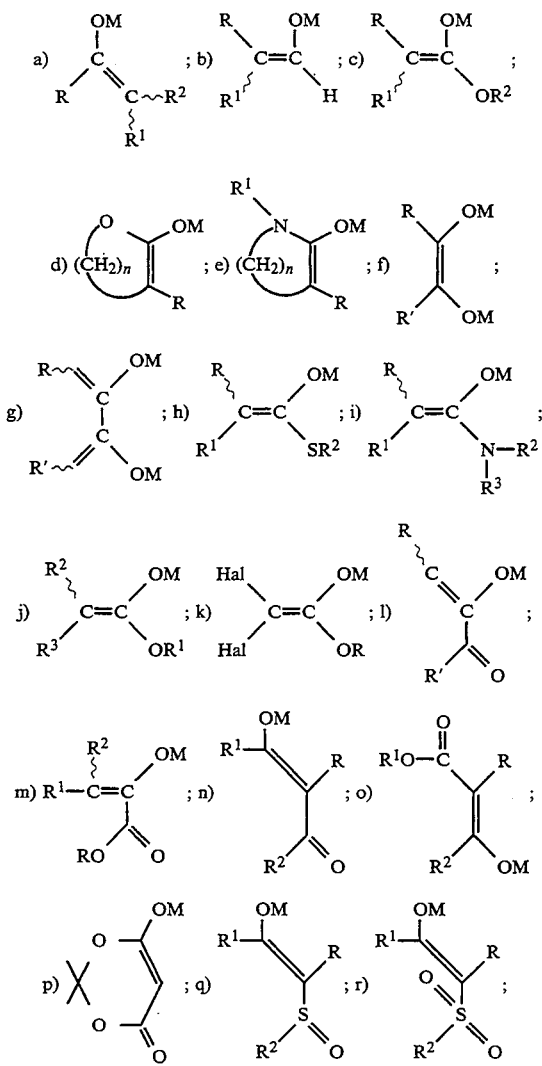

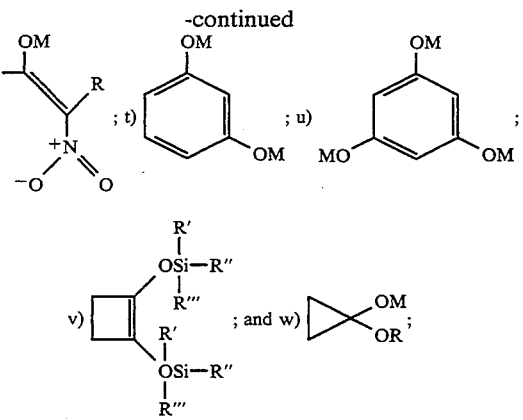

and allyl, vinyl, alkynyl and propargyl silanes and stannanes, and MCN; wherein M represents

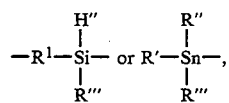

R, $R^1$ and $R^2$ are independently selected from alkyl, aryl, alkenyl and alkynyl, n is from 1 to 5, Hal is a halogen atom, and R', R" and R''' are independently selected from lower alkyl groups. Preferred nucleophiles are precursors of showdomycin, ravidomycin, formycin, and analogs thereof.

Thus, the soft nucleophiles include derivatives of enolates of ketone, aldehyde, ester, lactone, thioester, amides, and lactams, generally represented as RO—C(X)=C where X is a substituent and R is a trialkyl, dialkylaryl, and alkyldiaryl, or triarylsilyl or tin group, ketene acetals, 1,2- and 1,3-dicarbonyl compounds including Meldrum's acid and their derivatives, β-ketosulfoxides, β-ketosulfones, and β-ketonitro compounds and their derivatives, allyl, vinyl, aryl, alkynyl, and propargyl silanes and stannanes, silyl and stannyl cyanides (RR'R"SiCN and RR'R"SnCN), 1,3- and 1,3,5-dihydroxybenzene and their anion and per-trialkylsilyl and stannyl derivatives and their equivalents. Any of various suitable solvents can be used for the glycosylation reaction of which THF, acetone, diethyl ether, methylene chloride, chloroform, and benzene are preferred. The reaction temperature and time can be varied, e.g., ranging from −78° to room temperature for about 0.5 to 12 hours.

The following reactions in a preferred embodiment (Table 1) illustrate the invention.

TABLE I

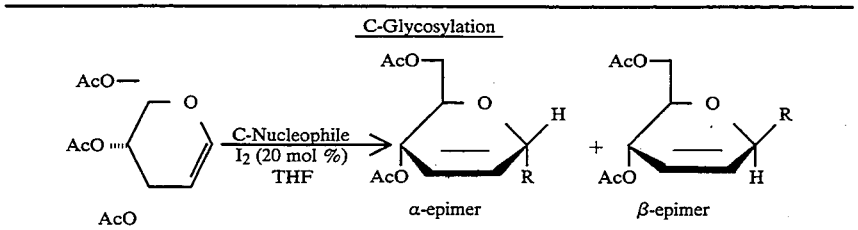

| C-Nucleophile | Temperature | Time | Products R | Yield | α:β |
|---|---|---|---|---|---|
| (CH$_3$)$_3$SiCH$_2$CH=CH$_2$ | −60° C. to RT | Overnight | —CH$_2$CH=CH$_2$ | 7-% | >20:1 |
| (CH$_3$)$_3$SiC≡N | −78° C. | 2 h | —C≡N | 75% | 3:1 |
| (CH$_3$)$_3$SiC≡N | −60° C. | 1 h | —C≡N | 78% | 1:3 |

TABLE I-continued

C-Glycosylation

| C-Nucleophile | Temperature | Time | Products R | Yield | α:β |
|---|---|---|---|---|---|
| ![OSi(CH3)3 phenyl vinyl] | −78° C. | 2 h | —CH₂C(=O)—Ph | 65% | 6:1 |
| ![OSi(CH3)3 phenyl vinyl] | −50° C. to RT | 12 h | —CH₂C(=O)—Ph | 78% | 2.7:1 |
| ![OSi(CH3)3 cyclohexenyl] | 50° C. to 0° C. | 2 h | 2-oxocyclohexyl | 65% | 4:1 |

RT = room temperature

As shown in the table, the epimeric ratio as well as preference for one of the two epimers of the C-glycosylated products is dependent on the temperature of the reaction (see the cases of trimethylsilyl cyanide and acetophenone trimethylsilyl ether). Moreover, quite significantly, the thermodynamically more favored β-epimer obtained from ketone enol silyl ethers can be obtained as a major product upon treatment of the initial α-epimer enriched product mixture with acid (as described by Kende, A. S.; Fujii, Y. *Tetrahedron Lett.* 1991, 32, 2199–2202) or base (as described by Dawe, R. D.; Fraser-Reid, B. *J.C.S. Chem. Commun.* 1981, 1180–1181 incorporated by reference) (see Scheme 1 below). The present invention in one preferred aspect includes the treatment of the α-epimer enriched product mixture with acid or base thus favoring the yield in the present method of the β-epimer, and making the present C-glycosylation even more versatile. Many of the present C-glycosylated products, particularly those with 1β-carbon chains are key intermediates in the synthesis of various C-glycoside antibiotics (as described in the two reviews cited above, incorporated herewith by reference).

SCHEME 1

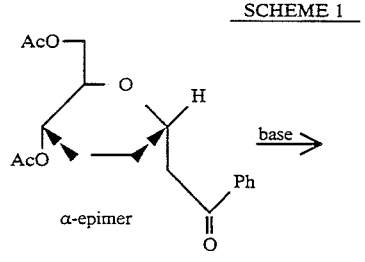

α-epimer

-continued
SCHEME 1

β-epimer

In another preferred aspect, the invention concerns partly and completely deacylated products having enhanced water-solubility, produced by hydrolysis of one or more acyl groups from the acylated product. For hydrolysis, acyl group removal can be achieved for example by refluxing the acylated product, under per se commonly used conditions for hydrolysis and workup, with an aqueous metal hydroxide (MOH; M=Li, K, Na) in methanol or ethanol, or with Zn (OAc)₂.2H₂O in methanol, or with LiAlH₄ or diisobutylaluminum hydride in benzene, toluene, ether or THF.

The invention and the best mode of carrying out the same are illustrated by the following non-limitative examples.

EXAMPLE I

Reaction of Triacetyl D-Glucal With Acetophenone Enol Trimethylsilyl Ether

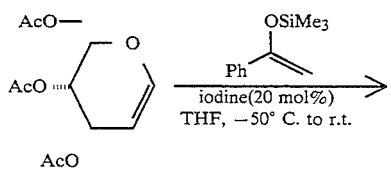

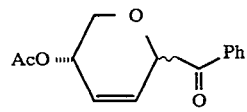

Triacetyl D-glucal (1.98 mmol) and iodine (0.398 mmol) were dissolved in 10 mL of THF and the solution was cooled to −50° C. To this solution was added acetophenone enol trimethylsilyl ether (2.00 mmol) and the reaction mixture was allowed to warm slowly to room temperature over 12 hours. The reaction mixture was then diluted with 50 mL of ether and the resulting solution was washed with 10 mL of 10% aqueous $Na_2S_2O_3$. The aqueous layer was back-extracted with ether (3×10 mL). The combined organic layers were dried over sodium sulfate and the solvent was evaporated in vacuo. The crude product thus obtained was purified by silica gel flash column chromatography (gradient elution with 9/1 to 2/1 hexanes/ethyl acetate), providing 1.55 mmol of the C-glycosylated product (78%) as a mixture of C-1 epimers (2.7:1α:β). For the major product α-epimer: $^1H$ NMR (300 MHz; $CDCl_3$) δ2.03 (s,3H), 2.09 (s,3H), 3.15 and 3.48 (AB quartet, 2H, $J_{AB}$=16.4 Hz; the 3.15 and 3.48 ppm peaks are further split into doublets with J=6.5 Hz and 7.1 Hz, respectively), 4.13 and 4.25 (AB quartet, 2H, $J_{AB}$=11.9 Hz; the 4.13 and 4.25 ppm peaks are further split into doublets with J=3.6 Hz and 6.6 Hz, respectively), 4.91–4.97 (m,1H), 5.13–5.17 (m,1H), 5.85 and 6.08 (AB quartet, 2H, $J_{AB}$=10.4 Hz; the 5.85 and 6.08 ppm peaks are further split into dd with J=3.0, 2.0 Hz and 2.5, 1.5 Hz, respectively). $^{13}C$ NMR (75.4 MHz; $CDCl_3$) δ20.70 (q), 21.05 (q), 42.70 (t), 63.25 (t), 65.51 (d), 68.99 (d), 71.04 (d), 124.84 (d), 128.90 (d), 129.38 (d), 133.56 (d), 133.96 (d), 137.98 (d), 137.98 (s), 171.03 (s), 171.42 (s), 197.99 (s).

EXAMPLE II

Reaction of Triacetyl D-Glucal With Allyltrimethylsilane

The procedure of Example I was followed except that the reaction was initiated at −60° C. and the reaction mixture was left at room temperature overnight. The 1-allyl product was obtained in 70% yield with over 20:1 α/β stereoselectivity. For the major α-epimer: $^1H$ NMR (300 MHz; $CDCl_3$) δ2.08 (s,6H), 2.27–2.36 (m,1H), 2.41–2.52 (m,1H), 3.93–4.02 (m,1H), 4.15 and 4.23 (AB quartet, 2H, $J_{AB}$=11.9 Hz; the 4.15 and 4.21 ppm peaks are further split into doublets of doublets with J=3.5 and 6.6 Hz, respectively), 4.25–4.31 (m,1H), 5.09–5.17 (m,3H), 5.76–5.89 (m,1H), 5.79 and 5.93 (AB quartet, 2H, $J_{AB}$=10.4 Hz; the 5.7 9 and 5.93 ppm peaks are further split into dd with J=2.8, 1.9 and 2.4, 1.6 Hz, respectively); $^{13}C$ NMR (75.4 MHz; $CDCl_3$) δ20.73, 21.00, 37.96, 62.94, 65.13, 70.00, 71.35, 117.44, 123.75, 132.83, 133.97, 170.24, 170.55.

EXAMPLE III

Reaction of Triacetyl D-Glucal With 1-Trimethylsilyloxy-1-cyclohexene

The procedure of Example I was followed except that the reaction was performed at −78° C. for 2 hours. The 1-(2-oxocyclohexyl) product was obtained in 65% yield with over 4:1 α/β stereoselectivity. For the major α-epimer: $^1H$ NMR (360 MHz; $CDCl_3$) δ2.08 (a,3H), 2.11 (s,3H), 2.30–2.43 (m,3H), 2.61–2.65 (m,1H), 3.86 (ddd, 1H, J=6.7, 6.7, 3.6 Hz), 4.16 and 4.24 (AB quartet, 2H, $J_{AB}$=11.9 Hz; the 4.16 and 4.24 ppm peaks are further split into doublets with J=3.6 and 6.8 Hz, respectively), 4.46 (ddd, 1H, J=8.8, 4.5, 2.3 Hz), 5.11–5.16 (m,1H), 5.77 and 6.14 (AB quartet, 2H, $J_{AB}$=10.5 Hz; the 5.77 and 6.14 ppm peaks are further split into doublets of doublets with J=2.9, 2.0 and 2.7, 1.5 Hz, respectively); $^{13}C$ NMR (75.4 MHz; $CDCl_3$) δ20.82, 21.06, 24.67, 27.94, 30.30, 42.74, 53.41, 62.92, 65.04, 70.15, 70.27, 123.56, 133.06, 170.34, 170.75, 210.95.

The procedure of Example 1 can be used for preparation of the stereoselective 2,3,5-triacetylribosylation of acid-sensitive substrate compounds such as precursors of the known compounds showdomycin, ravidomycin, formycin and like pharmacologically useful compounds. For example, the synthesis of glycosylated showdomycin can be accomplished using the commercially available soft carbon nucleophile 1,2 bis(trimethylsilyl)oxy-1-cyclobutene for stereoselective addition of a glycal selected from glycals of formula I–III and Ia–IIIa to produce an adduct which is converted to the target compound which can be deacylated by per se known procedures to provide showdomycin. A similar synthesis is reported in the Hacksell and Daves review article, supra, at page 43. The resulting novel triacetylribosylated substrate compounds are contemplated to have substantial advantage with respect to greater water solubility and yet have substantially the same useful antineoplastic activity and posology as the known compounds.

Having described the invention, the embodiments of the invention in which an exclusive property or privilege is claimed are defined as follows.

We claim:

1. A process for preparing C-glycoside compounds comprising reacting a soft carbon nucleophile and a glycal selected from acylated, carbonated and thionocarbonated five- and six-membered glycals in the presence of a catalytic amount of iodine to provide a reaction mixture containing the corresponding C-1α and C-1β glycosylated C-glycoside epimers, isolating at least one or both of said α and β epimers stereoselectively from said mixture, and optionally removing one or more acyl groups from said epimer products, wherein the soft carbon nucleophile comprises a compound or a moiety selected from members of the group consisting of enolate derivatives having the formulas a) to w)

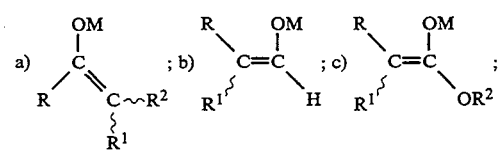

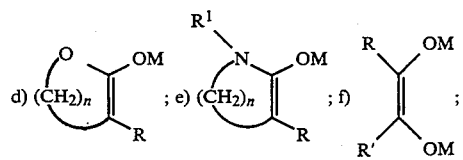

-continued

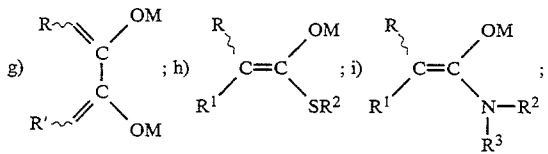

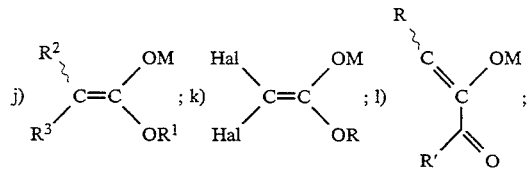

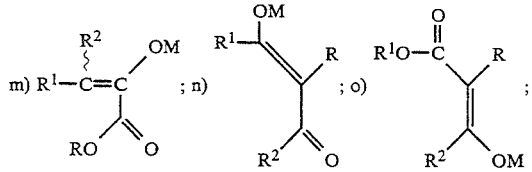

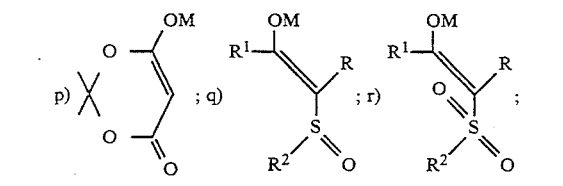

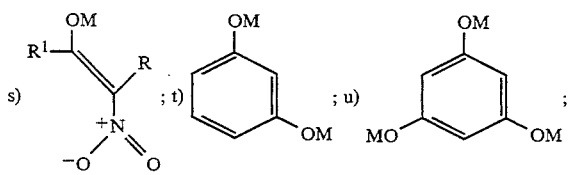

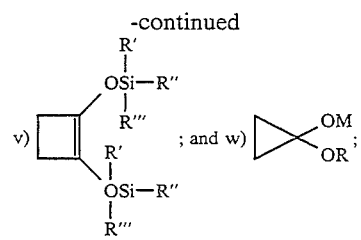

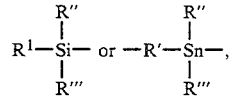

and allyl, vinyl, alkynyl and propargyl silanes and stannanes, arid MCN; wherein M represents $$R^1-\underset{\underset{R'''}{|}}{\overset{\overset{R''}{|}}{Si}}- \text{ or } -R'-\underset{\underset{R'''}{|}}{\overset{\overset{R''}{|}}{Sn}}-,$$

R, $R^1$ and $R^2$ are independently selected from alkyl, aryl, alkenyl and alkynyl, n is from 1 to 5, Hal is a halogen atom, and R', R" and R'" are independently selected from lower alkyl groups.

2. A process according to claim 1 wherein the glycal is a tri-acyl D-glucal.

3. A process according to claim 1 wherein the soft carbon nucleophile contains an acid-labile structural unit.

4. A process for preparing C-glycoside compounds comprising reacting a soft carbon nucleophile and a glycal selected from acylated, carbonated and thionocarbonated five- and six-membered glycals in the presence of a catalytic amount of iodine to provide a reaction mixture containing the corresponding C-1α and C-1β glycosylated C-glycoside epimers, isolating at least one or both of said α and β epimers stereoselectively from said mixture, and optionally removing one or more acyl groups from said epimer products, wherein the soft carbon nucleophile comprises a compound or a moiety selected from the group consisting of derivatives of enolates of ketone, aldehyde, ester, lactone, thioester, amides, and lactams generally represented as RO—C(X)=C where X is a substituent and R is a trialkyl dialkylaryl, and alkyldiaryl, or triarylsilyl or tin group, ketene acetals, 1,2- and 1,3-dicarbonyl compounds including Meldrum's acid and their derivatives, β-ketosulfoxides, β-ketosulfones, and β-ketonitro compounds and their derivatives, allyl, vinyl, aryl, alkynyl, and propargyl silanes and stannanes, silyl and stannyl cyanides (RR'R"SiCN and RR'R"SnCN), 1,3- and 1,3,5-dihydroxybenzene and their anion and per-trialkylsilyl and stannyl derivatives and their equivalents.

* * * * *

UNITED STATES PATENT AND TRADEMARK OFFICE
CERTIFICATE OF CORRECTION

PATENT NO. : 5,414,074          Page 1 of 4
DATED     : May 9, 1995
INVENTOR(S) : Koreeda et al.

It is certified that error appears in the above-indentified patent and that said Letters Patent is hereby corrected as shown below:

Column 2, line 38, delete " 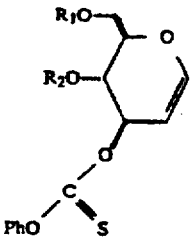 " and insert 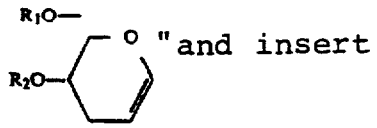

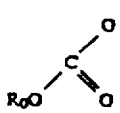

Column 2, line 47, delete " 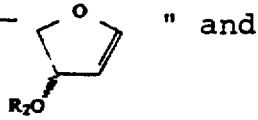 " and insert 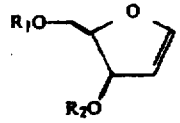

Column 2, line 53, delete "  " and insert 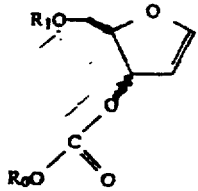

UNITED STATES PATENT AND TRADEMARK OFFICE
CERTIFICATE OF CORRECTION

PATENT NO. : 5,414,074
DATED : May 9, 1995
INVENTOR(S) : Koreeda et al.

It is certified that error appears in the above-indentified patent and that said Letters Patent is hereby corrected as shown below:

Column 4, line 23, delete " 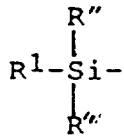 " and insert

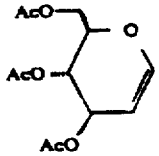

Column 4, Table I, delete " 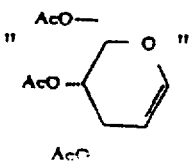 " and insert

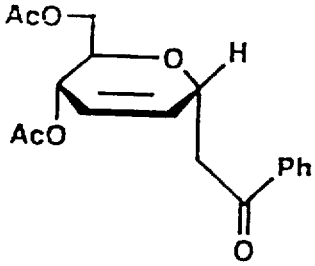

Column 4, Table (column yield) I, delete "7-%" and insert --70%--.

Column 5, Scheme 1, delete " 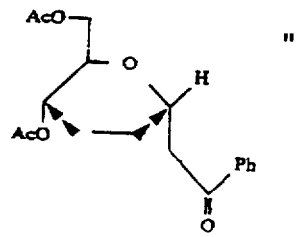 " and insert

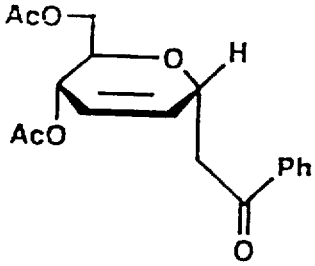

UNITED STATES PATENT AND TRADEMARK OFFICE
CERTIFICATE OF CORRECTION

PATENT NO. : 5,414,074   Page 3 of 4
DATED : May 9, 1995
INVENTOR(S) : Koreeda et al.

It is certified that error appears in the above-indentified patent and that said Letters Patent is hereby corrected as shown below:

Column 6, Scheme 1, delete " 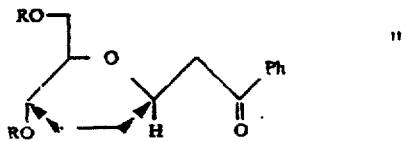 "
and insert 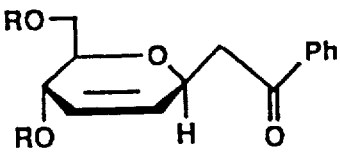

Column 6, line 63, delete " 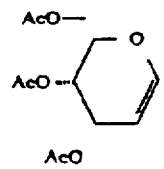 " and insert 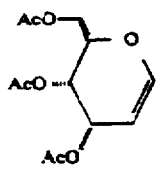

Column 2, line 20, delete " 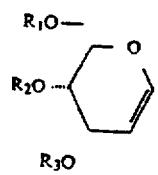 " and insert 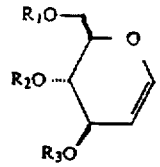

Column 2, line 28, delete " 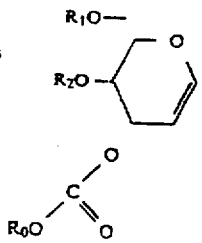 " and insert 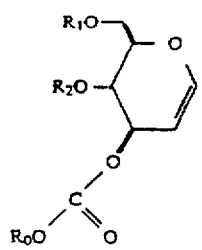

UNITED STATES PATENT AND TRADEMARK OFFICE
CERTIFICATE OF CORRECTION

PATENT NO. : 5,414,074
DATED : May 9, 1995
INVENTOR(S) : Koreeda et al.

It is certified that error appears in the above-indentified patent and that said Letters Patent is hereby corrected as shown below:

Column 2, line 63, delete " 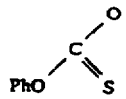 " and insert 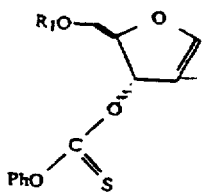

Column 7, line 5, delete " 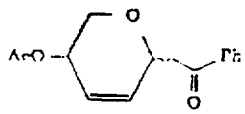 " and insert 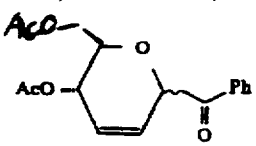

Signed and Sealed this

Seventh Day of November, 1995

Attest:

BRUCE LEHMAN

Attesting Officer

Commissioner of Patents and Trademarks